(12) United States Patent
Kauchali

(10) Patent No.: US 8,691,881 B2
(45) Date of Patent: Apr. 8, 2014

(54) CONVERSION OF CARBON CONTAINING FEEDSTOCK

(75) Inventor: Shehzaad Kauchali, Johannesburg (ZA)

(73) Assignee: University of the Witwatersrand, Johannesburg (ZA)

( * ) Notice: Subject to any disclaimer, the term of this patent is extended or adjusted under 35 U.S.C. 154(b) by 0 days.

(21) Appl. No.: 13/504,851

(22) PCT Filed: Oct. 28, 2010

(86) PCT No.: PCT/IB2010/054887
§ 371 (c)(1),
(2), (4) Date: Jul. 13, 2012

(87) PCT Pub. No.: WO2011/051902
PCT Pub. Date: May 5, 2011

(65) Prior Publication Data
US 2012/0277328 A1    Nov. 1, 2012

(30) Foreign Application Priority Data
Oct. 28, 2009  (ZA) .................................. 2009/07556

(51) Int. Cl.
*C07C 27/00*    (2006.01)

(52) U.S. Cl.
USPC ........... 518/704; 518/700; 518/702; 518/703; 518/705

(58) Field of Classification Search
USPC ................................................ 518/700–705
See application file for complete search history.

(56) References Cited

U.S. PATENT DOCUMENTS

| 2003/0115800 | A1  | 6/2003  | Yamada et al. |
| 2003/0236312 | A1  | 12/2003 | O'Rear |
| 2007/0124997 | A1  | 6/2007  | Liu et al. |
| 2007/0225383 | A1* | 9/2007  | Cortright et al. .............. 518/702 |
| 2008/0115415 | A1* | 5/2008  | Agrawal et al. ................. 48/101 |
| 2008/0237542 | A1  | 10/2008 | Schmidt et al. |
| 2009/0077892 | A1* | 3/2009  | Shulenberger et al. ....... 48/62 R |

FOREIGN PATENT DOCUMENTS

| CN | 10055082      | 10/2008 |
| CN | 101289373     | 10/2008 |
| WO | 2006100572 A1 | 9/2006  |
| WO | 2008010994 A2 | 1/2008  |

OTHER PUBLICATIONS

PCT/IB2010/054887 International Search Report, mailed Jun. 4, 2011.
PCT/IB2010/054887 Written Opinion (PCT Rule 66), mailed Jun. 12, 2011.
PCT/IB2010/054887 Int'l Preliminary Report on Patentability, completed Mar. 12, 2012.

* cited by examiner

*Primary Examiner* — Jafar Parsa
(74) *Attorney, Agent, or Firm* — Cooley LLP

(57) ABSTRACT

This invention relates to a process for the conversion of carbon containing feedstock to a liquid chemical product, particularly a liquid fuel product, wherein carbon dioxide emissions are minimized.

7 Claims, 5 Drawing Sheets

CONVERSION OF CARBON CONTAINING FEEDSTOCK

CROSS REFERENCE TO RELATED APPLICATIONS

This application is a National Stage Application filed under 35 U.S.C. §371 for PCT Application No. PCT/IB2010/054887, filed Oct. 28, 2010, entitled, "Conversion of Carbon Containing Feedstock", which claims priority to ZA Patent Application No. 2009/07556, filed Oct. 28, 2009, both of which are incorporated herein by reference in their entireties.

FIELD OF THE INVENTION

This invention relates to conversion of carbon containing feedstock to other materials such as liquid chemicals and fuels. In particular, this invention relates to a process for producing a liquid chemical or fuel product wherein $CO_2$ emissions are minimised.

BACKGROUND TO THE INVENTION

In the conversion of carbon containing feedstock to other materials, traditional conversion plants are synonymous with the incorporation of processes that invariably lead to the production of carbon dioxide ($CO_2$), a green house gas.

For example, in Fischer-Tropsch processes a set of chemical reactions convert a mixture of carbon monoxide (CO) and hydrogen gas ($H_2$) into liquid hydrocarbons ($CH_2$). The CO and $H_2$ are, initially, produced by an endothermic reaction of a carbon containing feedstock such as, for example, coal (C) with steam ($H_2O$) and oxygen ($O_2$) as represented by the following gasification process:

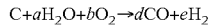

$$C + aH_2O + bO_2 \rightarrow dCO + eH_2$$

The CO is then partially converted to $CO_2$ and $H_2$ by the following water gas shift process in order to achieve a desired carbon monoxide to hydrogen gas ratio (synthesis gas ratio):

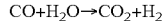

$$CO + H_2O \rightarrow CO_2 + H_2$$

The water gas shift process is controlled so as to provide the required $CO:H_2$ molar ratio for the Fischer-Tropsch process in which synthesis gas is further reacted to a myriad of chemicals and fuels. Typically the $CO:H_2$ molar gas ratio is 1:2. However, excess $CO_2$ is generated in the gas shift process and has to be removed from the system via a gas cleaning step which is undesirable and costly.

This process also requires a considerable amount of energy input to drive the endothermic reaction.

It is thus an object of this invention to address at least some of the abovementioned problems.

SUMMARY OF THE INVENTION

According to the invention there is provided a process for producing a liquid chemical or fuel product wherein $CO_2$ emissions are minimised, the process including reacting a carbon-containing feedstock in a reaction with an oxygen-containing gas and a co-feed substance which is describable in a C—H—O ternary phase diagram and which lies in a region bound by $CH_2$—$H_2O$—$H_2$ points on said diagram.

According to a first embodiment of the invention there is provided for the reaction to occur in a single vessel, to be overall thermally balanced, to require minimal $O_2$, and to produce minimal or no $CO_2$. Preferably, $H_2O$ is added as reagent to the reacting carbon-containing feedstock, oxygen-containing gas, and co-feed substance.

There is further provided for the reaction to operate on, or very close to, a boundary line linking $CH_2$ and $H_2O$ on the C—H—O ternary phase diagram.

Moreover, there is provided for the product to be synthesis gas; alternatively, dimethyl ether; further alternatively, a Fisher-Tropsch fuel product. The process may also be arranged to produce a Fisher-Tropsch fuel product, $H_2O$, and unconverted synthesis gas, wherein the unconverted synthesis gas may be combusted in a turbine to generate electricity.

According to a second embodiment of the invention there is provided for multiple reactions to occur in multiple vessels, a first vessel being arranged to subject the carbon-containing feedstock, in a first reaction, to a gasification reaction which is thermally balanced.

In accordance with an aspect of this embodiment of the invention, $H_2O$ is, preferably, added as reagent to the first reaction. Further preferably, $CO_2$ is added as reagent to the first reaction. The reagents $H_2O$ and $CO_2$ may be sourced via recycling from reaction products of a further reaction or reactions occurring in a further vessel or vessels.

In accordance with an additional aspect of this embodiment of the invention, there is provided for the product to be synthesis gas; alternatively, dimethyl ether; further alternatively, a Fisher-Tropsch fuel product.

According to a third embodiment of the invention there is provided for multiple reactions to occur in multiple vessels, a primary vessel being arranged to subject the carbon-containing feedstock, in a primary reaction, to an endothermic gasification reaction that thermally balances a further reaction or reactions occurring in a further vessel or vessels and which is/are exothermic so that the overall process for producing a liquid chemical or fuel product is thermally balanced.

In accordance with an aspect of this embodiment of the invention, the primary reaction is a synthesis gas producing reaction and the further reaction is a dimethyl ether producing reaction, said reactions overall being thermally balanced.

In accordance with an additional aspect of this embodiment of the invention, the primary reaction is a synthesis gas producing reaction, the further reaction is a dimethyl ether producing reaction, and the yet further reaction is a desired Fisher-Tropsch fuel producing reaction, said reactions overall being thermally balanced.

In accordance with a further aspect of this embodiment of the invention, $H_2O$ is, preferably, added as reagent to the primary reaction. Further preferably, $CO_2$ is added as reagent to the primary reaction. The reagents $H_2O$ and $CO_2$ may be sourced via recycling from reaction products of the further reaction or reactions occurring in a further vessel or vessels.

There is also provided for the carbon-containing feedstock to be selectable from the group consisting of coal, petroleum refinery residue, biomass and waste.

In a particular embodiment of the invention there is provided for the co-feed substance to be methane, alternatively, hydrogen gas. The oxygen-containing gas may either be air, enriched air or oxygen.

BRIEF DESCRIPTION OF THE DRAWINGS

The invention is now described by way of example with reference to the accompanying non-limiting diagrammatic drawings. In the drawings.

DETAILED DESCRIPTION OF THE INVENTION

In the conversion of carbon containing feedstock such as coal to other materials, a ternary carbon/hydrogen/oxygen phase diagram is particularly useful. Use of such a diagram allows one to plot compositions as bond-equivalent percentages, i.e. with each element given a weighting appropriate to its power of combining with the other elements.

Figure 1:
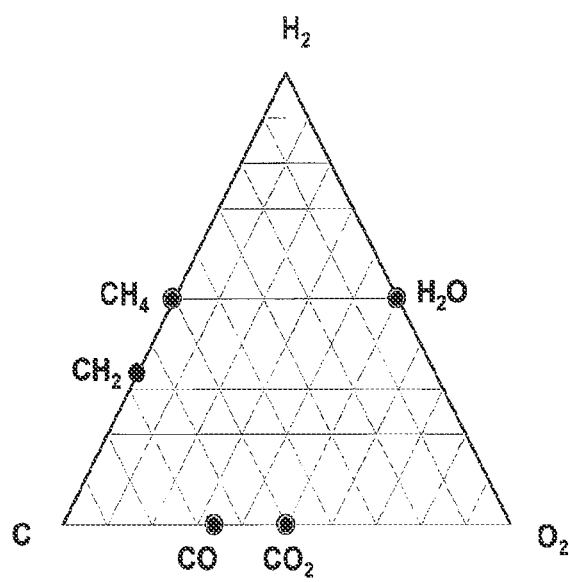
FIG. 1 shows a typical ternary C—H—O phase diagram that can be used in embodiments of the invention.
Figure 2:
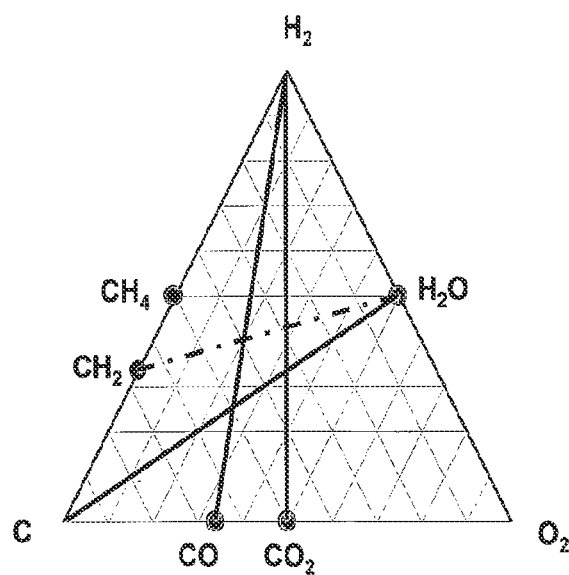
FIG. 2 shows a graphical representation of chemical species on a C—H—O bond equivalent phase diagram.

The diagram thus allows one to represent the various process steps in fuel production thereon. As shown in FIG. 1 C, O$_2$, H$_2$, CO, CO$_2$, CH$_4$, CH$_2$ & H$_2$O bond equivalent mole fractions may be present. At the apexes of the phase diagram appear C, O$_2$ and H$_2$ and any point, in the interior, represents any real molecule comprising C—H—O. Various boundaries can be created by joining the components by straight lines as shown in FIG. 2. These lines represent important physiochemical unit operations such as mixing, reaction or separation.

Traditional processes using natural gas (methane) have the potential of producing liquid fuels or chemicals whilst producing the least CO$_2$ to the environment. It is this salient feature of CH$_4$ that is exploited in this invention to obviate any CO$_2$ produced using coal.

An important overall process may be summed as C+aCH$_4$+bO$_2$-->dCH$_2$+eH$_2$O. The mixing of a co-feed substance allows for the feed, to the process, to lie closely on the line joining the CH$_2$ and H$_2$O points and it is noted that the process does not produce CO$_2$. This is quite different from the traditional coal processes where the overall processes may be represented by 3C+2H$_2$O-->2CH$_2$+CO$_2$ or 3C+4H$_2$O-->2CH$_2$+2H$_2$O+CO$_2$ which inherently produce CO$_2$.

Referring to FIG. 2, of particular interest are the Carbon-Steam, H$_2$—CO, H$_2$—CO$_2$ boundary lines. In order to minimise, or eliminate CO$_2$-rejecting processes it is imperative to operate on, or very close to, the CH$_2$—H$_2$O boundary line which represents the products of typical FT processes. Processes operating on this boundary do not require the rejection of CO$_2$ in the lever-arm rule but instead reject H$_2$O.

Figure 3:
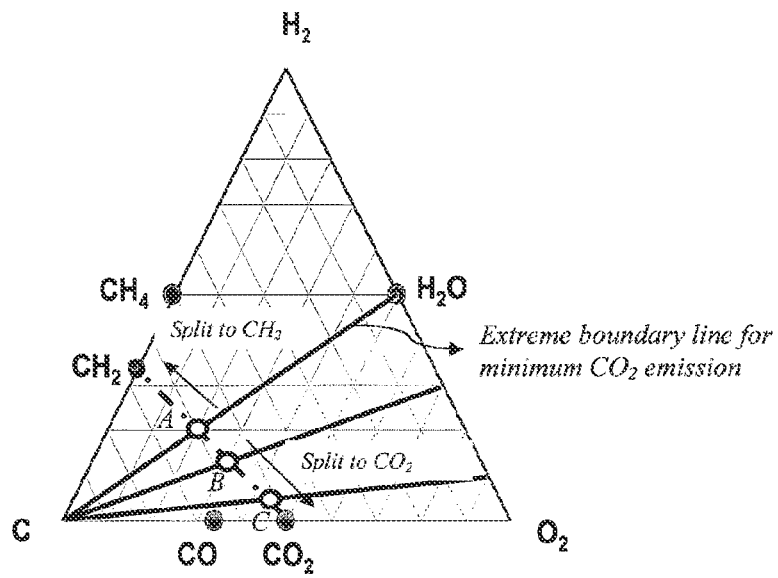
FIG. 3 shows a graphical representation of various feeds (C, H$_2$O & O$_2$ only) and minimum CO$_2$ emissions on the C—H—O bond equivalent phase diagram.

FIG. 3 represents three feed conditions (A,B,C) which represent various ratios of C:H$_2$O:O$_2$ and lie between the CH$_2$—CO$_2$ line. It can be shown that if coal is used as the only feedstock with steam and oxygen (Point A) then the carbon-steam boundary line represents the extreme operating condition for minimum CO$_2$ rejection. If any other point (e.g. B or C) are used then from the lever-arm rule more CO$_2$ will be emitted as the feed points are getting closer to the CO$_2$ point. Moreover, CO$_2$ rejection is inevitable in such processes as the lever-arm rule requires both CO$_2$ and fuels (CH$_2$) to be produced on either side of the straight line. Operating, strictly, within the region described by C—H$_2$O—O$_2$ points (shaded region) will require CO$_2$ rejection greater than the minimum achieved on the boundary of C—H$_2$O.

Co-Feed Substance/Agent

Figure 4:
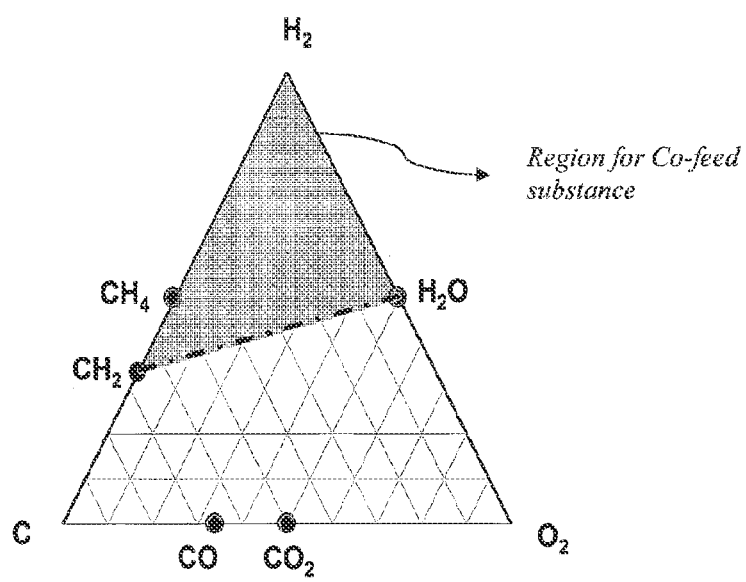
FIG. 4 shows a region, on the C—H—O bond equivalent phase diagram, containing choice for a co-feed substance in accordance with the invention.

In order to minimise, or eliminate CO$_2$-rejecting processes it is imperative to operate on, or very close to, the CH$_2$—H$_2$O boundary line which represents the products of typical FT processes as shown in FIG. 4. Processes operating on this boundary do no require the rejection of CO$_2$ in the lever-arm rule but instead reject H$_2$O.

The invention thus uses methane (as co-feed substance), for example and carbon feedstock, for the production of liquid chemicals and fuels, in such proportions that avoids overall CO$_2$-rejecting fundamental processes. In principle, any other available substance can be added to carbon containing feed on condition that it is describable in the CHO phase diagram and is above the CH$_2$—H2O boundary line. Another possible agent, if produced economically, is hydrogen.

A region can now be defined (shaded in FIG. 4) as being bound by CH$_2$—H$_2$O—H$_2$ that allows any combination of co-feed substance to be added to the coal in order to bring the overall feed composition on the CH$_2$—H$_2$O line. For example, we could use CH$_4$ to add with C and H$_2$O to obtain an operating point producing synthesis gas comprising of CO and H$_2$ in the ratio 1:2, as required for FT. If H$_2$ is available, as a cheap resource, then a linear combination of C, H$_2$ and H$_2$O could be used to produce the syngas anywhere on the CH$_2$—H$_2$O boundary to feed into the FT reactor. Any feed or combinations of co-feeds in the CH$_2$—H$_2$O—H$_2$ region can be used with coal to allow the operation on the CH$_2$—H$_2$O line and thus eliminate CO$_2$ production.

Here, the processes are multiple steps that do not include external pre-heating of the feedstock with combustible fuels that are secondary sources of CO$_2$ (in addition to CO$_2$ formed due to O$_2$ production).

Dimethyl-ether (DME), a clean diesel-substitute, is traditionally produced from the dehydration of methanol. However, there are methods that use syngas (CO:H$_2$=1:2), produced from the partial oxidation of methane, directly to DME (with methanol production as intermediate step). DME may also be produced from coal where syngas with ratio CO:H$_2$=1:1 is used. The advantage of this process is that it has a higher equilibrium conversion than using a higher CO:H$_2$ (1:2) and separation of DME from CO$_2$ is fairly easy. However, producing DME from coal only results in the formation of large amounts of CO$_2$ in the DME reactor as well as the gasifier. The key advantage of producing DME, amongst others, is that it is also a feedstock to FT products. This is achieved by further dehydrating DME over appropriate catalyst to the desired FT fuels. The resulting fuels do not require intense refinery steps as in conventional FT processes.

Incorporating CH$_4$ in coal gasification and operating at thermally neutral conditions for the production of liquid chemicals and fuels has several advantages. Firstly, a potent green-house gas is removed from the environment and no CO$_2$ is released in return, less of the expensive oxygen is required and more fuel can be produced per mol of carbon in the feed than the traditional coal-steam method.

The invention will now be described and exemplified by way of specific examples which are not intended to limit the invention in any way, but which are provided only to describe specific preferred embodiments of the invention.

EXAMPLE 1

One-Step Processes & Fuels/Chemicals Production

It is noted that $CO_2$ recycling processes and gasification and fuel production reactions may be incorporated into a single process. It is acknowledged that these processes are indeed catalytically controlled and may require further development in order to function simultaneously at the same reaction temperature. For example, the operating temperature may require high temperature FT catalyst and low temperature catalyst to produce the synthesis gas ("syngas") in the gasification process. It is not the objective here to develop catalyst for this process but to highlight the need to develop the catalyst in order to perform the one-step process efficiently. The advantages of operating a one step process include: 1) equipment reduction 2) no external recycling 3) ease of final product separation 4) potential use of air instead of pure oxygen (i.e. no air separation required) 5) simultaneous sulphur (or other catalyst poisoning) cleaning 6) No intermediate $CO_2$ removal step required.

The endothermic reaction in the gasification and the exothermic reaction in the fuel process may occur in an overall thermally balanced manner. This would, for example, require a fixed bed of coal blended with the bi-functional catalyst (or mix of catalyst) which would be fluidised (or non-fluidised) with a mix of methane, oxygen or steam to produce dimethyl ether ("DME") or a desired Fisher-Tropsch ("FT") fuel product (for ease of reference referred to herein further as "$CH_2$"). The reactions can also occur in a slurry bed reactor where coal and catalyst are dispersed in an inert liquid and the reactive gases are bubbled through the bed.

In the examples below, it should be noted that necessary gas cleanup steps, prior to catalyst usage, have been omitted. Furthermore, it is assumed that the feed to the processes are received at the appropriate temperatures and pressures required for further processing.

EXAMPLE 1.1

One-Step Process: FT Production

The endothermic reaction in the gasification and the exothermic reaction in the FT process are shown below:

Gasification:

$$CH_4 + 1.118C + 0.118O_2 + 1.882CO_2 \xrightarrow{Q_1} 4(CO + 0.5H_2) \quad (375.1 \text{ kJ/mol})$$

FT Production:

$$4(CO + 0.5H_2) \xrightarrow{Q_2} 2CH_2 + 2CO_2 \quad (-375.1 \text{ kJ/mol})$$

The two processes may occur in a single vessel thereby operating in an overall thermally balanced manner. The overall thermally balanced single-step process is given by $$CH_4 + 1.118C + 0.118O_2 \xrightarrow{Q_1} 2CH_2 + 0.118CO_2 \quad (0 \text{ kJ/mol})$$

It is noted that enriched air (less $N_2$) or air may be used. However, the system may have to run slightly exothermically to account for the presence of inert nitrogen in the system as well as to pre-heat the feed to reaction temperatures.

EXAMPLE 1.2

One-Step Process: DME Production with Oxygen/Air

The endothermic reaction in the gasification and the exothermic reaction in the DME process are shown below:

Gasification:

$$CH_4 + 0.501C + 0.75CO_2 + 0.249O_2 + 0.252H_2O \xrightarrow{Q_1} 2.252(CO + H_2) \quad (184.2 \text{ kJ/mol})$$

DME Production:

$$2.252(CO + H_2) \xrightarrow{Q_2} 0.75C_2H_6O + 0.75CO_2 \quad (-184.2 \text{ kJ/mol})$$

The two processes may occur in a single vessel thereby operating in an overall thermally balanced manner. The overall thermally balanced single-step process is given by $$CH_4 + 0.501C + 0.249O_2 + 0.252H_2O \xrightarrow{Q_1} 0.75C_2H_6O \quad (0 \text{ kJ/mol})$$

This reaction scheme requires only the addition of methane, steam and oxygen to coal. It is noted that no $CO_2$ is formed from the overall single process as it is consumed internally in the gasification reaction.

If pure oxygen is used, then pure DME may be formed. It is noted that enriched air (less $N_2$) or air may be used. However, the system may have to run slightly exothermically to account for the presence of inert nitrogen in the system.

Most DME catalysts operate optimally at around 550K. This either requires that efficient gasification catalyst be obtained to operate at 550K to produce syngas ($CO:H_2=1:1$) or develop a DME catalyst to operate at higher temperatures. However, the DME equilibrium drops considerably at higher temperatures and may be required to operate at high pressures in order to increase equilibrium conversions.

EXAMPLE 1.3

One-Step Process: DME & FT Production

It is possible that an additional catalyst be added in the blend to dehydrate DME to FT products. This would, in principle, be a tri-catalyst system enabling the internal recycling of $CO_2$ as well as $H_2O$. For example if we consider the DME system that requires oxygen then the overall process is $$CH_4 + 0.501C + 0.249O_2 \xrightarrow{Q_1} 1.5CH_2 + 0.489H_2O \quad (\text{exothermic})$$

The feed to the system here is only methane, oxygen and coal. It is noted that the feed lies on the line joining $CH_2$ and $H_2O$ on the bond equivalent phase diagram. The reaction is overall exothermic since the FT catalyst has been added on an existing thermally balanced DME operation.

A tri-catalyst system may operate overall thermally neutrally according to the overall reaction below:

$$CH_4 + 0.795C + 0.102O_2 \xrightarrow{Q_1} 1.795CH_2 + 0.205H_2O \quad (0 \text{ Kj/mol})$$

This system requires the DME reaction to produce the $CO_2$ as well as the FT reaction to form the $H_2O$ required to feed the endothermic gasification process internally. The heat from both the DME and FT process drives the endothermic reaction in an overall thermally balanced manner. It is further noted that operation in this method requires the least oxygen and produces the least waste water and more hydrocarbons per mol methane.

EXAMPLE 2

Thermally Balanced Operations for Gasification Processes

It is common practice to operate gasification processes near thermally balanced conditions. This condition is achieved when the endothermic reactions (see FIG. 5) are simultaneously driven by a set of exothermic reactions within the gasifier.

Figure 5:
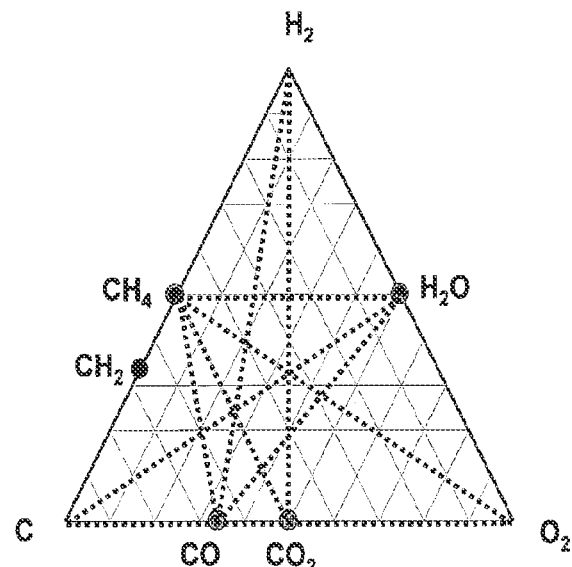
FIG. 5 shows a graphical representation of important gasification reactions on the C—H—O bond equivalent phase diagram.

The important reactions can thus be represented graphically on the bond equivalent phase diagrams as points of intersection between the various species as shown in FIG. 5. For example the intersection of the carbon-steam line and the $CO-H_2$ line represents the reaction $C+H_2O \rightarrow CO+H_2$ or may also represent $2C+2H_2O \rightarrow CH_4+CO_2$. For downstream processes the former gas (syngas) is more desirable as an intermediate.

EXAMPLE 2.1

Thermally Balanced Operations for Gasification Processes: Coal & Methane Processes Methane and coal can be reacted thermally neutrally, in a gasifier, to obtain a gas with a $CO_2:H_2$ ratio=1:3. The advantage of using this stoichiometry is in the fact that the gasifier operates directly on the line linking $CH_2-H_2O$. The thermally balanced reaction, G, is given by G:$CH_4$+0.2109C+0.3946$O_2$+
1.6325$H_2O \rightarrow$ 1.211$CO_2$+3.632$H_2$ (0 kJ/mol)

This reaction uses a relatively significant amount of coal with the methane. However, a large amount of water is also required, but may be offset by recycling.

Figure 6:
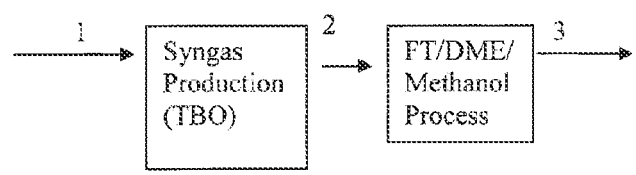
FIG. 6 shows a process flowsheet for fuel or chemical production from CO$_2$ and H$_2$ gases according to an embodiment of the invention.

The $CO_2-H_2$ rich gas may be used directly as feed for methanol, DME or FT. The overall process is shown in FIG. 6, and Table 1 represents the mole balances for the process.

TABLE 1

Mole balances for $CO_2:H_2 = 1:3$

| Component | 1 | 2 | 3 (methanol) | 3 (FT) | 3 (DME) |
|---|---|---|---|---|---|
| C | 0.2109 | | | | |
| O2 | 0.3946 | | | | |
| H2O | 1.6325 | | 1.211 | 2.422 | 1.816 |
| CH4 | 1 | | | | |
| H2 | | 3.632 | | | |
| CO2 | | 1.211 | | | |
| CO | | | | | |
| C2H6O | | | | | 0.605 |
| CH3OH | | | 1.211 | | |
| CH2 | | | | 1.211 | |

TABLE 2

Products Formed per mole methane in Feed

| | Amount (per mol CH4 in feed) | | | | | |
|---|---|---|---|---|---|---|
| Methanol Process | | FT Process | | DME Process | | |
| CH3OH | 1.211 | CH2 | 1.211 | C2H6O | 0.605 |
| H2O | 1.211 (zero if recycled) | H2O | 2.422 (0.789 if recycled) | H2O | 1.816 (0.1839 if recycled) |

The distinct advantage of this process is that no $CO_2$ is formed and that a reasonable amount of coal is used relative to the methane. However, methane is still considered to be the dominant amount in the overall feed. This process might be of particular interest for isolated coal mines that produce captured methane. The captured methane with low grade, unwashed coal and air can be used to produce liquid fuels, which can be transported via conventional methods. Here the methane is thus converted to fuels without methane or $CO_2$ emissions.

EXAMPLE 2.2

Thermally Balanced Operations for Gasification Processes: Coal & Methane with $CO_2$ Recycle Process for Direct FT Here we consider the case where we determine the parameters a,b,d,e and f for the following reaction so that the overall heat of reaction is zero and maximum $CO_2$ is used

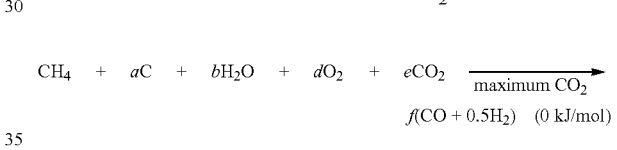

The resulting thermally balanced solution is given by reaction A, below:

A:$CH_4$+2.068C+1.068$O_2$+0.932$CO_2 \rightarrow$ 4(CO+0.5$H_2$) (0 kJ/mol)

Notice that there is no steam required for this particular CO:$H_2$=1:0.5 ratio. The syngas produced can further react to form FT products as shown (in an exothermic reaction)

4(CO+0.5$H_2$) $\rightarrow$ 2$CH_2$+2$CO_2$

Figure 7:
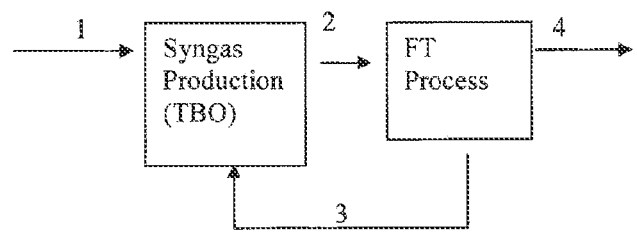
FIG. 7 shows a process flowsheet for Fisher Tropsch (FT) production from recycled CO$_2$ according to an embodiment of the invention.

The $CO_2$ formed in the FT process is recycled to the thermally balanced gasifier. The overall process is shown in FIG. 7, and Table 3 represent the mole balances for the process.

TABLE 3

Mole balances for FT with $CO_2$ recycle

| Component | 1 | 2 | 3 | 4 |
|---|---|---|---|---|
| C | 2.068 | | | |
| O2 | 1.068 | | | |
| H2O | | | | |
| CH4 | 1 | | | |
| H2 | | 2 | | |
| CO2 | | | 0.932 | 1.068 |
| CO | | 4 | | |
| C2H6O | | | | |
| CH3OH | | | | |
| CH2 | | | | 2 |

TABLE 4

Products Formed per mole methane in Feed for FT
Amount (per mol CH4 in feed)

| FT Process | | DME Process | |
|---|---|---|---|
| CH2 | 2 | C2H6O | — |
| CO2 | 1.068 | CO2 | — |

EXAMPLE 2.3

Thermally Balanced Operations for Gasification Processes: Coal & Methane with $CO_2$ Recycle Process for FT via DME Here we consider the case where we determine the parameters a,b,d,e and f for the following reaction so that the overall heat of reaction is zero and maximum $CO_2$ is used

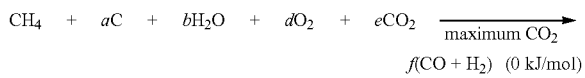

$$CH_4 + aC + bH_2O + dO_2 + eCO_2 \xrightarrow[\text{maximum } CO_2]{} f(CO + H_2) \quad (0 \text{ kJ/mol})$$

The resulting thermally balanced solution is given by reaction C, below:

C: $CH_4 + 0.634C + 0.634O_2 + 0.366CO_2 \rightarrow 2(CO+H_2)$ (0 kJ/mol)

The syngas further reacts to form DME according to

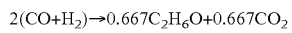

$2(CO+H_2) \rightarrow 0.667C_2H_6O + 0.667CO_2$

DME is further dehydrated to FT products and water

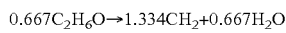

$0.667C_2H_6O \rightarrow 1.334CH_2 + 0.667H_2O$

Figure 8:
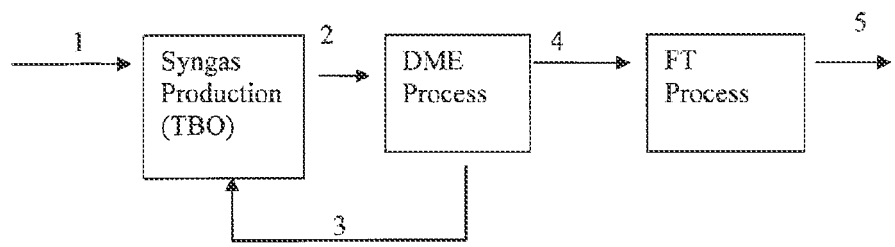
FIG. 8 shows a process flowsheet for FT production via dimethyl ether (DME) with recycled CO$_2$ according to an embodiment of the invention.

The flowsheet is shown in FIG. 8 below. The mole balances are given in Tables 5 and 6. The $CO_2$ in stream 4 is removed prior to FT processing.

TABLE 5

Mole balances for FT via DME

| Component | Stream (mol/s) | | | | |
|---|---|---|---|---|---|
| | 1 | 2 | 3 | 4 | 5 |
| C | 0.634 | | | | |
| O2 | 0.634 | | | | |
| H2O | | | | | 0.667 |
| CH4 | 1 | | | | |
| H2 | | 2 | | | |
| CO2 | | | 0.366 | 0.3 | 0.3 |
| CO | | 2 | | | |
| C2H6O | | | | 0.667 | |
| CH3OH | | | | | |
| CH2 | | | | | 1.334 |

TABLE 6

Products Formed per mole methane in Feed for FT via DME
Amount (per mol CH4 in feed)

| FT Process | | DME Process | |
|---|---|---|---|
| CH2 | 1.334 | C2H6O | — |
| CO2 | 0.3 | CO2 | — |
| H2O | 0.667 | H2O | — |

EXAMPLE 3

Non-Thermally Balanced Operations for Gasification Processes

Figure 9:
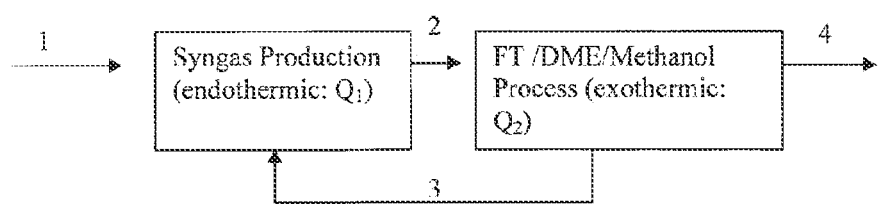
FIG. 9 shows a process flowsheet for fuel/chemical production with recycled CO$_2$ according to an embodiment of the invention.

In this example we remove the requirement that the gasification occurs under thermally balanced conditions. Here, we let the gasification occur sufficiently endothermically so that the exothermic fuel/chemical production step is precisely matched and the overall process is thermally balanced. The advantage of operating in this mode enables operating the overall process with lower $CO_2$ production. The overall process flowsheet is given in FIG. 9.

It is noted that $Q_1 = -Q_2$ so that the overall process is thermally balanced and no excess heat is required to be added or removed from the process.

Table 7 below lists the heat of reaction for the compounds at 650K where $CH_2$ is represented by one eighth of octene $(C_8H_{16})$

TABLE 7

Heat of reaction (KJ/mol) for compounds at 650K

| Compound | Heat of Reaction (KJ/mol) |
|---|---|
| CH4 | −77.1 |
| H2O | −242.6 |
| CO | −110.9 |
| CO2 | −394.1 |
| DME (l) | −184.0 (298K) |
| CH2 (l) | −15.3 (298K) |

EXAMPLE 3.1

Non-Thermally Balanced Gasification Operation: FT Production

For the FT production, the reaction schemes that need to be determined are represented by A and B, below:

A:

$$CH_4 + aC + bH_2O + dO_2 + eCO_2 \xrightarrow{Q_1} f(CO + 0.5H_2) \quad (Q_1 \text{ kJ/mol})$$

B:

$$f(CO + 0.5H_2) \xrightarrow{Q_2} \frac{f}{2}CH_2 + gCO_2 \quad (Q_2 \text{ kJ/mol})$$

Hence, for $Q_1 = -Q_2$, the resulting reaction schemes are:

Gasification:

$$CH_4 + 1.118C + 0.118O_2 + 1.882CO_2 \xrightarrow{Q_1} 4(CO + 0.5H_2) \quad (375.1 \text{ kJ/mol})$$

FT Production:

$$4(CO + 0.5H_2) \xrightarrow{Q_2} 2CH_2 + 2CO_2 \quad (-375.1 \text{ kJ/mol})$$

The mole balances are given in Tables 8 and 9 below:

TABLE 8

Mole balances for FT (Non-thermally balanced gasifier)

| Component | Stream (mol/s) | | | |
|---|---|---|---|---|
| | 1 | 2 | 3 | 4 |
| C | 1.118 | | | |
| O2 | 0.118 | | | |
| H2O | | | | |
| CH4 | 1 | | | |
| H2 | | 2 | | |
| CO2 | | | 1.882 | 0.118 |
| CO | | 4 | | |
| C2H6O | | | | |
| CH3OH | | | | |
| CH2 | | | | 2 |

TABLE 9

Products Formed per mole methane in Feed for FT
FT Process (via DME)

| CH2 | 2 |
|---|---|
| CO2 | 0.118 |

EXAMPLE 3.2

Non-Thermally Balanced Gasification Operation: FT Production via DME

For the DME production the reaction schemes that need to be determined are represented by D and E, below:

D:

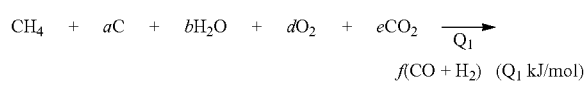
$CH_4 + aC + bH_2O + dO_2 + eCO_2 \xrightarrow{Q_1} f(CO + H_2)$ ($Q_1$ kJ/mol)

E:

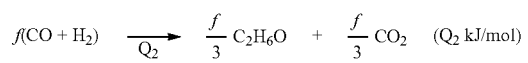
$f(CO + H_2) \xrightarrow{Q_2} \frac{f}{3} C_2H_6O + \frac{f}{3} CO_2$ ($Q_2$ kJ/mol)

Hence, for $Q_1 = -Q_2$, the resulting reaction schemes are:

Gasification:

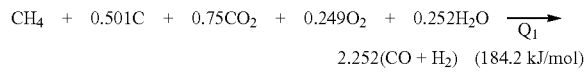
$CH_4 + 0.501C + 0.75CO_2 + 0.249O_2 + 0.252H_2O \xrightarrow{Q_1} 2.252(CO + H_2)$ (184.2 kJ/mol)

DME Production:

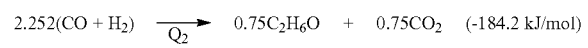
$2.252(CO + H_2) \xrightarrow{Q_2} 0.75C_2H_6O + 0.75CO_2$ (−184.2 kJ/mol)

This is followed by the dehydration of DME to FT products and H2O according to:

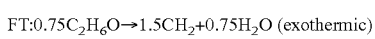
FT: $0.75C_2H_6O \rightarrow 1.5CH_2 + 0.75H_2O$ (exothermic)

Figure 10:
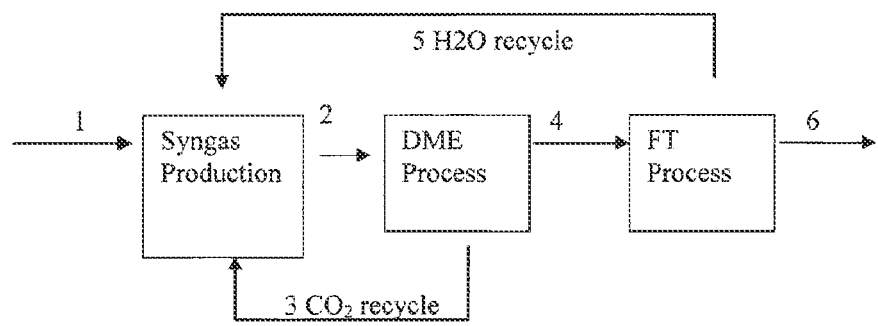
FIG. 10 shows a process flowsheet for FT production via DME with CO$_2$ and recycled H$_2$O according to an embodiment of the invention.

The H2O and CO2 are recycled and the process is shown in FIG. 10.

The mole balances are given in Tables 10 and 11 below.

TABLE 10

Mole balances for FT via DME (Non-thermally balanced gasifier)

| Component | Stream (mol/s) | | | | | |
|---|---|---|---|---|---|---|
| | 1 | 2 | 3 | 4 | 5 | 6 |
| C | 0.501 | | | | | |
| O2 | 0.249 | | | | | |
| H2O | | | | | 0.252 | 0.498 |
| CH4 | 1 | | | | | |
| H2 | | 2.252 | | | | |
| CO2 | | | 0.75 | | | |
| CO | | 2.252 | | | | |
| C2H6O | | | | 0.75 | | |
| CH3OH | | | | | | |
| CH2 | | | | | | 1.5 |

TABLE 11

Products Formed per mole methane in Feed for FT via DME
FT Process (via DME)

| CH2 | 1.5 |
|---|---|
| CO2 | 0 |
| H2O | 0.498 |

Table 12 shows the heat balance for the system that produces DME with oxygen in feed.

TABLE 12

Heat Balances for Gasification & DME process

| Process | Heat (KJ/s) |
|---|---|
| Gasification | 184.2 |
| DME process | −184.2 |

This particular system is of tremendous interest as there is no $CO_2$ formed by the overall process. All $CO_2$ that gets produced in the DME reactor is recycled and utilised in the gasifier with only FT (and $H_2O$) in the final product stream.

It is noted that the overall process here is exothermic and the feed (stream 1) lies on the line joining $CH_2$ and $H_2O$ on the bond equivalent phase diagram.

EXAMPLE 3.3

Non-Thermally Balanced Gasification Operation: FT Production via DME Overall Thermally Balanced For the FT production that is overall balanced, the reaction schemes that need to be determined are represented by D, E and F, below:

D:

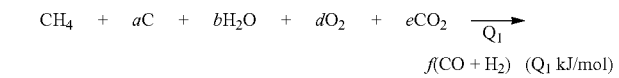
$CH_4 + aC + bH_2O + dO_2 + eCO_2 \xrightarrow{Q_1} f(CO + H_2)$ ($Q_1$ kJ/mol)

E:

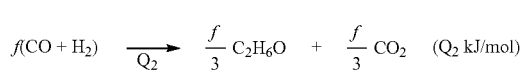
$f(CO + H_2) \xrightarrow{Q_2} \frac{f}{3} C_2H_6O + \frac{f}{3} CO_2$ ($Q_2$ kJ/mol)

F:

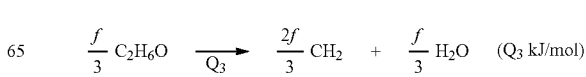
$\frac{f}{3} C_2H_6O \xrightarrow{Q_3} \frac{2f}{3} CH_2 + \frac{f}{3} H_2O$ ($Q_3$ kJ/mol)

Hence, for $Q_1=-Q_2-Q_3$, the resulting process reactions are $$CH_4 + 0.795C + 0.693H_2O + 0.102O_2 + 0.898CO_2 \xrightarrow{Q_1}$$
$$2.693(CO + H_2) \quad (300.3 \text{ kJ/mol})$$

$$2.693(CO + H_2) \xrightarrow{Q_2} 0.898C_2H_6O + 0.898CO_2 \quad (-220.3 \text{ kJ/mol})$$

$$0.898C_2H_6O \xrightarrow{Q_3} 1.795CH_2 + 0.898H_2O \quad (-80 \text{ kJ/mol})$$

The overall process is:

$CH_4+0.795C+0.102O_2 \rightarrow 1.795CH_2+0.205H_2O$ (0 Kj/mol)

The mole balances are given in Tables 13 and 14 below for a flowsheet similar to FIG. 10.

TABLE 13

Mole balances for FT via DME (Non-thermally balanced gasifier)

| Component | Stream (mol/s) | | | | | |
|---|---|---|---|---|---|---|
| | 1 | 2 | 3 | 4 | 5 | 6 |
| C | 0.795 | | | | | |
| O2 | 0.102 | | | | | |
| H2O | | | | | 0.693 | 0.205 |
| CH4 | 1 | | | | | |
| H2 | | 2.693 | | | | |
| CO2 | | | 0.898 | | | |
| CO | | 2.693 | | | | |
| C2H6O | | | | 0.898 | | |
| CH3OH | | | | | | |
| CH2 | | | | | | 1.795 |

TABLE 14

Products Formed per mole methane in Feed for FT via DME FT Process (via DME)

| CH2 | 1.795 |
|---|---|
| CO2 | 0 |
| H2O | 0.205 |

Table 15 below shows the heat balance for the tri-catalyst system that produces FT via DME.

TABLE 15

Heat Balances for Gasification, DME & FT process

| Process | Heat (KJ/s) |
|---|---|
| Gasification | 300.3 |
| DME process | −220.3 |
| FT process | −80.0 |

The invention claimed is:

1. A process for producing a liquid chemical or liquid fuel product wherein $CO_2$ emissions are minimized, the process comprising the steps of:
   (i) endothermically gasifying a carbon-containing feedstock with an oxygen-containing gas and a carbon-containing co-feed substance to form a synthesis gas, wherein the carbon-containing co-feed substance is a substance which lies in a region bound by points $CH_2$—$H_2O$—$H_2$ on a C—H—O ternary phase diagram;
   (ii) in the same vessel as the gasification reaction, exothermically reacting the synthesis gas to form dimethyl ether or a Fisher-Tropsch fuel product; and
   (i) recycling any CO2 within theprocess;
   wherein the use of the carbon-containing co-feed reduces the production of $CO_2$ in the process.

2. The process of claim 1, in which $H_2O$ is added as reagent to the reacting carbon-containing feedstock, oxygen-containing gas, and carbon-containing co-feed substance.

3. The process of claim 1, in which the process also produces $H_2O$, carbon dioxide and unconverted synthesis gas.

4. The process of claim 1, in which the process also produces unconverted synthesis gas.

5. The process of claim 1, wherein the endothermic reaction of step (i) and the exothermic reaction of step (ii) occur in a thermally balanced manner.

6. The process of claim 1 wherein the process is overall exothermic.

7. A process for producing dimethyl ether wherein $CO_2$ emissions are minimised, the process comprising the steps of:
   (i) endothermically gasifying a carbon-containing feedstock with an oxygen-containing gas and a carbon-containing co-feed substance to form a synthesis gas, wherein the carbon-containing co-feed substance is a substance which lies in a region bound by points $CH_2$—$H_2O$—$H_2$ on a C—H—O ternary phase diagram;
   (ii) in a separate vessel as the gasification reaction, exothermically reacting the synthesis gas to form dimethyl ether; and
   (iii) recycling any $CO_2$ within the process;
   wherein the use of the carbon-containing co-feed reduces the production of $CO_2$ in the process.

* * * * *